United States Patent [19]
Jubinsky

[11] Patent Number: 5,932,704
[45] Date of Patent: Aug. 3, 1999

[54] ANTIBODIES FOR GM-CSF RECEPTOR AND USES THEREOF

[75] Inventor: Paul T. Jubinsky, Boston, Mass.

[73] Assignee: Dana-Farber Cancer Institute, Boston, Mass.

[21] Appl. No.: 08/378,076

[22] Filed: Jan. 25, 1995

Related U.S. Application Data

[63] Continuation of application No. 07/977,757, Nov. 19, 1992, abandoned.

[51] Int. Cl.$^6$ .................................................. C07K 16/00
[52] U.S. Cl. ................................. 530/388.22; 530/388.7; 530/389.6; 435/7.24; 435/721; 436/548
[58] Field of Search .......................... 530/388.22, 388.7, 530/389.6; 435/7.24, 7.21, 240.27, 172.2; 436/548; 424/139.1, 143.1, 144.1, 181.1, 183.1, 9.1, 1.49

[56] References Cited

U.S. PATENT DOCUMENTS 5,629,283  5/1997  Nicola et al. ............................... 514/2

FOREIGN PATENT DOCUMENTS

| 0409091 | 1/1991 | European Pat. Off. |
| 91/01330 | 2/1991 | WIPO |
| 91/02063 | 2/1991 | WIPO |
| WO94/09149 | 4/1994 | WIPO |

OTHER PUBLICATIONS

Chiba, S. et al. Journal Biological Chemistry,265, No. 32:19777–19781 (Nov. 15, 1990).

Watanabe, W., et al., Blood 80, No. 9:2215–2220 (Nov. 1, 1992).

Sasaki, K., et al., Biochem. Biophys. Res. Commun. 183, No. 1:252–275 (Feb. 28, 1992).

Nicola, N.A., et al., Blood, 82, No. 6:1724–1731 (Sep. 15, 1993).

Harlow et al, 1988. *Antibodies. A Laboratory Manual*, Cold Spring Harbor Laboratory, Cold Spring Harbor, pp. 72–74.

Gearing et al, 1989. Expression cloning of a receptor for human granulocyte–macrophage colony–stimulating factor, EMBO J 8:3667–76.

Raines et al, 1991 (Sep.). Identification and moleular cloning of a soluble human granulocyte–macrophage colony-–stimulating factor receptor PNAS 88:8203–7.

Maurer et al, 1980. Proteins and polypeptide as antigens. Meth. Enzymol. 70:49–70.

Goding, 1983. *Monoclonal Antibodies: Principles and Practice*. Academic Press, Inc., Orlando. pp. 1–3, 40.

*Primary Examiner*—Carol A. Spiegel
*Assistant Examiner*—James L. Grun
*Attorney, Agent, or Firm*—Ronald I. Eisenstein; David G. Conlin

[57] ABSTRACT

Antibodies capable of binding to the a subunit of the human GM-CSF receptor are described. These antibodies can inhibit the proliferation of cells whose growth is dependent upon the presence of human GM-CSF. Methods of assaying for the human GM-CSF receptor are also disclosed.

6 Claims, 4 Drawing Sheets

ANTIBODIES FOR GM-CSF RECEPTOR AND USES THEREOF

This is a continuation of application Ser. No. 07/977,757 filed on Nov. 19, 1992, now abandoned.

The present invention is directed to the detection and quantification of human granulocyte-macrophage colony stimulating-factor (GM-CSF) receptors in body tissues or body fluids, isolation of cells expressing such receptors, detection and quantification of such receptors as well as therapy using such antibodies.

GM-CSF can be expressed by a variety of cell types including T cells, macrophages, mast cells, endothelial cells and fibroblasts, in response to specific activating signals such as immune or inflammatory stimuli. GM-CSF is a hematopoietic growth factor that can stimulate the proliferation of granulocyte, macrophage, erythrocyte, megakaryoycte and eosinophil progenitors in vitro [Metcalf, D., et al., *Blood* 55: 137–147 (1980)]. In addition, it has been shown to regulate granulocyte levels in vivo [Donahue, R. E., et al., *Nature* 321:872–75 (1986); Mayer, P., et al., *Blood* 70:206–213 (1987); Antman, K. S., et al., *New Eng. J. Med.* 319:593–598 (1988)]. Furthermore, many of the primary myeloid leukemic blasts that form colonies in vitro are dependent on its presence or that of other crude sources of hematopoietic growth factors for proliferation [Griffin, J. D., et al., *Blood* 67:1448–1453 (1986); Hoang, T., et al., *Blood* 68:313–316 (1986)]. It has been reported that in certain cases where blasts of patients secrete GM-CSF, antibodies to GM-CSF have inhibited proliferation [Young, D. C., et al., *Blood* 68:1178–1181 (1986)]. Furthermore, myeloproliferation in juvenile chronic myelogenous leukemia appears to be due to sensitivity of the leukemic blasts to GM-CSF [Emmanuel, P. D., *Exp. Hematol.* 19:1017–1024 (1991)]. Thus, the expression of GM-CSF appears to play a roll in pathogenic processes. In addition to the aforementioned role in primary myeloid leukemia cells and neoplasia, the protein has also been shown to be expressed by certain solid tumors. The protein is present in synovial fluid from patients with inflamatory arthropathies such as rheumatoid arthritis [Alvaro-Garcia, J. M., et al., *J. Immun.* 146:3365–3371 (1991)].

GM-CSF binds to a receptor known as the GM-CSF receptor. The receptor is a member of a highly conserved cytokine receptor super family [Cosman D. et al., *Trends Biochem. Sci.* 15:265–270 (1990)]. These receptors has been found on carcinoma lung cell lines, human endothelial cells, human placenta, trophoblast cells, melanoma tumor cells lines, etc. [Baldwin, G. C., et al. *Blood* 78:609–615 (1991)].

The receptor is comprised of two subunits which result in different affinities for GM-CSF observed on some hematopoietic cells [Walker & Burges, *EMBO J.* 4:933–9 (1985); Nimmer S. D. et al. *Year in Immunol.* 3:144–57 (1988)]. The first chain is commonly referred to as the $\alpha_1$ subunit, and is an 85 Kd which can bind GM-CSF by itself with low affinity. [Gearing, D. P., et al., *EMBO J.* 8:3667–3676 (1989)]. There are two other α isoforms, a soluble form [Raines, J. A., et al., *Proc. Natl. Acad. Sci. USA* 88:8203–8207 (1991)], the other, $\alpha_2$, is identical to $\alpha_1$, except for the terminal 35 amino acids of the cytoplasmic region. The extracellular portion of the chain is highly glycosylated. The receptor has a second subunit, the β chain, which does not bind to GM-CSF by itself. Rather, it will bind GM-CSF when associated with the $\alpha_1$ receptor. This α/β receptor complex binds GM-CSF with high affinity. The β subunit is 135 Kd and can also serve as the second subunit for interleuken receptors such as Il-3 and Il-5 [Hayashida, K. et al., *Proc. Natl. Acad. Sci., USA,* 87:9655–9659(1990); Kitamura, T. et al., *Cell* 66:1165–1174(1991)]; Tavernier, J., et al., *Cell* 66:1175–1184 (1991)].

Other members of this family include receptors for G-CSF, growth hormone, Interleukin-3 (Il-3) Il-4, Il-6, Il-7, murine erythropoietin, human IL-2 receptor β-chain and the rat prolactin receptor. While these receptors do not contain a kinase domain such as exist in other receptors there are a number of conserved amino acid residues within this family including four cysteine residues and a region immediately extracellar of the trans-membrane domain [Gasson, J. C., *Blood* 77:1131–1145 (1991)].

It would be desirable to have a method of quantitatively measuring the amount of the GM-CSF receptor expressed.

It would also be desirable to have a method of measuring the presence of this receptor on specific cell lines.

SUMMARY OF THE INVENTION

We have now generated, isolated and characterized antibodies which will specifically bind to the a subunits of the human GM-CSF receptor. These antibodies can be used to detect human GM-CSF receptors on cells, in bodily fluids or on tissues. These antibodies can also be used to tag the soluble form of the a receptor. For example, one can detect either form of the receptor, i.e. the a subunit of receptor bound to the cell or the soluble form, by reacting a fluid or tissue sample with the antibodies described herein or an immunoreactive fragment, thereof. Immunoblot and immunoassays using the antibody or such immunoreactive fragments, described above are also disclosed. The bodily fluid or tissue samples can be removed from a patient and the receptor assayed in vitro, or one can inject labelled antibody into a patient and then scan for accumulation of the labelled antibody.

The antibody can also be conjugated to a delivery system to deliver a desired molecule to a target.

DETAILED DESCRIPTION OF THE INVENTION

Detailed Description of the Invention

Figure 1A:
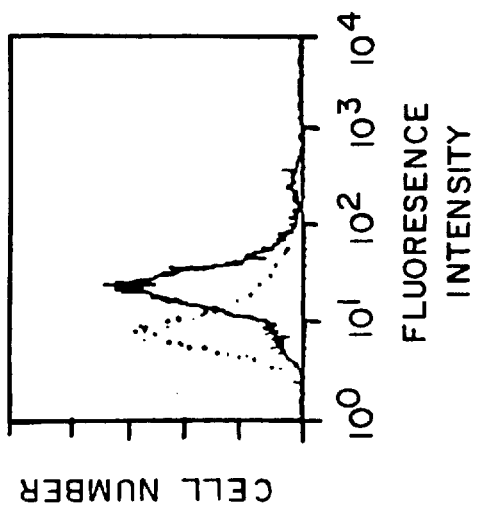
FIGS. 1A–1C show a FACS analysis of an antibody according to the present invention binding to FDCP1 cells.

The antibodies described herein will bind to the a subunits of the GM-CSF receptor, which is preferably an 84 kD glycoprotein, preferably the $\alpha_1$ subunit. The α glycoprotein can range in weight from about 40 kD to about 85 kD. Preferably the α glycoprotein is from about about 50 to about 85 kD, more preferably about 75 to about 85 kD. Still more preferably, the a subunit is about 84 kD. The antibody will bind to the protein in its native configuration and under relatively mild denaturation conditions. The antibody will also recognize both other α isoforms, namely a truncated soluble form of the $\alpha_1$ receptor as well as the $\alpha_2$ subunit.

The presently described antibodies can be either monoclonal or polyclonal antibodies, although monoclonal antibodies are preferred. Furthermore, as used herein, the term antibody includes whole immunoglobulin as well as antigenic binding fragments (i.e. immunoreactive fragments) thereof, which display the above-described binding characteristics. For example, it includes the portion of the antibody that will bind to the protein, such as a Fab sequence or an Fv sequence. Although the smallest fragment that contains a complete binding site is the Fv fragment, antigen binding activity can be obtained with only a heavy chain binding domain and such a fragment is included as long as it has a binding affinity to the α subunit of at least about $10^{-7}$, more preferably at least about $10^{-8}$. An antibody comprised of at least the Fv fragment is preferred.

The antibody is preferably generated to a native GM-CSF receptor, although one can prepare an immunogenic peptide that has the basic conformational structure of a desired epitope on an α subunit, such as the $α_1$ subunit of the GM-CSF receptor and use that to generate the antibody. Such peptides [Chiba, S., et al. *Cell Reg.* 1:327–335 (1990); Onetto-Pothier, N., et al., *Blood* 75:59–66 (1990)] can be synthesized by conventional means. For example, one can clone the α receptor or screen for cells expressing the α receptor. Preferably, one transforms a cell line with a vector encoding the α subunit receptor. The transformed cells are then selected by standard means. The cell line is preferably from the host being used to generate the antibody. Typically the vector used also contains a selectable marker so one can readily determine that the cell has been transformed. Alternatively, one can use labelled human GM-CSF to screen for cells expressing the receptor. The cells expressing the α receptor are then preferably rescreenned to obtain those cells expressing high levels of receptor. For example, one can subject the cells to fluorescence activated cell sorting (FACS) with a labelled GM-CSF, for example phycoerythrin-labelled hGM-CSF. Cells expressing high levels of the α receptor are collected, incubated and resorted several times, e.g. 3 times, to obtain cells expressing very high levels of receptor.

The antibodies can be prepared by techniques well known to the skilled artisan. For example, cells having the receptor protein, the protein or an antigenic portion thereof can be conjugated to keyhole limpet hemocyanin (KLH) and used to raise an antibody in an animal such as a rabbit. Preferably, one uses the whole cell with a high level of receptors on it. Typically the peptide-KLH conjugate is injected several times over a period of about two months to generate antibodies. Antibodies are collected from serum by standard techniques and screened to find an antibody specific for the external portion of the receptor. Monoclonal antibodies can be produced in cells which produce antibodies and used to generate monoclonal antibodies by using standard fusion techniques for forming hybridoma cells [Kohler, G., et al. *Nature* 256:495 (1975)]. Typically this involves fusing an antibody producing cell with an immortal cell line such as a myeloma cell to produce the hybrid cell. Alternatively, monoclonal antibodies can be produced from cells by the method of Huse, et al., *Science* 246:1275 (1989), both Kohler and Huse are incorporated herein by reference.

For example, hybridomas can be generated by immunization of mice with viable cells expressing the GM-CSF receptor. Preferably, these cells express the full length protein, although partial domains can also be used. Using the full length protein as an immunogen, it is possible to generate a collection of monoclonal antibodies with specificities that span the entire length of the protein. This is as opposed to the use of peptide immunogens or short polypeptides generated by prokaryotic systems, which present a more limited number of epitopes from the original protein and hence raise an immune response of more limited specificity. Furthermore, the protein should not be fully denatured.

The mice, for example, DBA/2 mice or SJL mice, can be immunized intraperitoneally (I.P.) with a sufficient number of viable cells of the host cell, which expresses high levels of the α subunit receptor. The injection scheme used can be determined based upon the host. For example, i.p. injection without adjuvant into the DBA/2 mice every 4–6 weeks for a series of injections. Preferably, one would use 3–6 injections. One can check anti-α titer on the α receptor by FACS to see if the level of antibody produced is sufficient. With the injected SJL mice a cyclophosphamide injection intraperitonially can be done one and two days following the primary injection. About two weeks following immunization, mice are then injected with a sufficient amount of cells expressing high levels of GM-CSF receptor and then allowed another two weeks at which time the entire procedure is repeated. Alternatively, with for example SJL mice, there can be 12 I.P. injections of different types of cells, which, however, express the receptor, every 1–2 weeks. This would be followed with a single large injection of receptor expressing cell. Four days following the last injection of the transformed cells, the animals are sacrificed and their spleens obtained for the first fusion.

Hybridomas are produced by fusing cells by standard techniques, such as from immunized mice with SP2/0 myeloma cells by a polyethylene glycol (PEG) method. Cells are asceptically removed from immunized mice and a single cell suspension of the spleen cells obtained by perfusing the spleen with serum-free media (e.g., DMEM). Spleen cells and myeloma cells are mixed together at a ratio, for example, of 5 to 1, spleen cells to myeloma cells. The cells are then centrifuged and the supernatant removed by aspiration. The cells are then grown in medium by standard techniques. Hybridomas, which grow after the fusion procedure, are then screened for secretion of antibodies which show high levels of binding to cells having GM-CSF receptors and not receptor-free parental cells. Screening can be done on fixed cells or cell lysates or by cell surface immunofluorescence staining of live cells. Hybridomas that produce positive results are expanded and cloned by limiting dilution to assure that the cells and resulting antibodies are indeed monoclonal. Hybridoma colonies that test positive for these characteristics and presumably the presence of antibody to GM-CSF receptor are diluted in media to a concentration of, for example, 0.5 hybridoma cells per milliliter. Once colonies grow, the supernatants are again tested for the presence of antibody to the receptor. If the results are positive when tested by an ELISA assay, the colonies are cloned again by limiting dilution.

Preferred monoclonal antibodies include 1.013A, 207E1, 4A4C1, 11E7A1, and 12E7A1 which are mouse monoclonal antibody directed to the external portion of the receptor. Hybridomas expressing these monoclonal antibodies have been deposited with the American Type Culture Collection (ATCC), 10801 University Boulevard, Manassas, Va. 20110-2209 and given Accession Nos. HB 11198, HB 11194, HB 11195, HB 11197 and HB 11196, respectively.

Figure 1B:
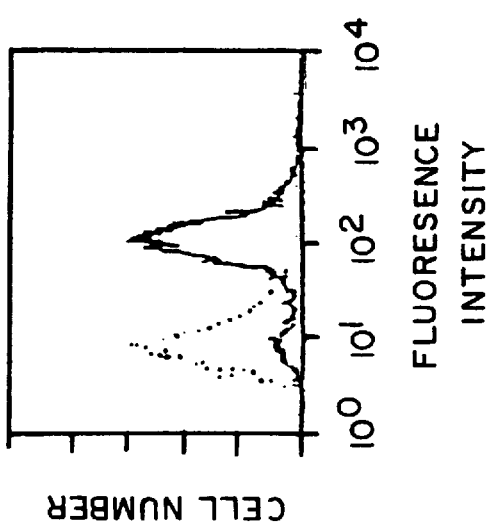
Figure 1C:
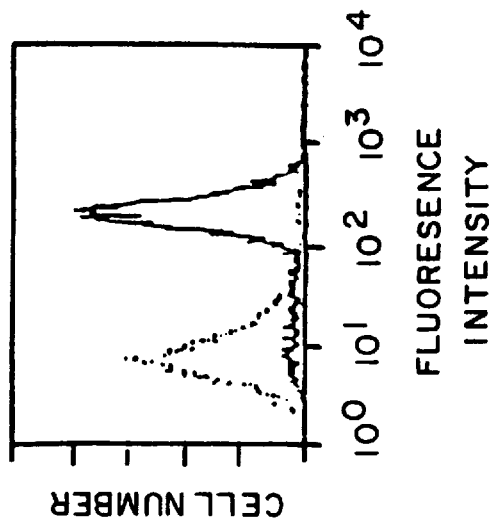

We have prepared at least three different types of antibodies. These antibodies are specific for the alpha chain of the human GM-CSF receptor. These antibodies provide three different types of interaction as measured by FACS. FIG. 1 shows FDCP1 [Dexter, T. M., et al., *J. Exp. Med.* 152:1036–1047 (1980)] cells express high levels of the recombinant GM-CSFα receptor (solid line) and wild type FDCP1 cells not expressing receptor (dotted line) incubated with tissue culture supernatent from hybridoma cells which produce anti GM-CSF antibodies for one hour at 4°. Three different levels of binding are observed. In FIG. 1A a low level of binding; while FIG. 1B shows a medium level, and FIG. 1C shows a high level of binding. All the cells were washed and incubated with label, for example, fluorescein label goat antimouse Ig Fab$_2$ fragment before being subjected to FACS analysis.

Such results suggest that there are three classes of antibody affinity, three different receptor epitopes or different forms of the receptor such as glycosylation differences or conformational changes induced by other subunits or proteins. Although not wishing to be bound by theory, we believe that it is the result of three different antibody affinities.

These antibodies are also able to inhibit the proliferation of cells that are dependent on the presence of hGM-CSF, and hence its effect on a cell. For example, the growth of human GM-CSF dependent cell lines such as TF-1 and MO7 and murine factor dependent cell lines, such as FDCP1 and Ba/F3, that express a functional human GM-CSR receptor in the presence of human GM-CSF but not interleukin-3 (IL-3). This inhibition of effect can be shown using crude or purified antibodies individually or a pool of the antibodies. Although single antibodies can be used, in certain embodiments one preferably uses a cocktail (pool) of such antibodies that bind to different epitopes to obtain the inhibition of proliferation effect. For example, the binding of a GM-CSF, such as a labelled GM-CSF such as $^{125}$I-GM-CSF, is blocked by such a pool. See, FIG. 2 which measures a cell line having high receptor expression such as FDCP1 cells expressing human GM-CSF receptor alpha subunits. When such cell line was incubated in the presence of specified concentration of the labelled GM-CSF with or without a 150 fold excess of unlabelled GM-CSF, with or without pooled antibody, for example 30 μg/ml, for an appropriate temperature for a sufficient time such as five hours at 4° C., the amount of antibody can be determined by standard techniques such as for example centrifuging of cells through 100% fetal calf serum with the pellet counted by use of a gamma camera. The results are set forth in the table below.

TABLE 1

| $^{125}$I-GM-CSF (M) | Specific Binding (cpm)[a] | Specific Binding[b] with Antibody (cpm) | % Inhibition[c] |
|---|---|---|---|
| 1.0 × 10$^{-9}$ | 1930 | 430 | 76 |
| 5.0 × 10$^{-9}$ | 1342 | 407 | 70 |
| 2.5 × 10$^{-10}$ | 318 | 82 | 75 |

[a]Specific binding = cpm bound minus cpm bound in the presence of unlabeled ligand.
[b]Specific binding with antibody - cpm bound in the presence of antibody minus cpm bound in the presence of antibody and unlabeled ligand.
[c]% decrease in $^{125}$I-GM-GSF binding caused by the antibodies.

In another embodiment the antibodies can be used to screen for cells expressing human GM-CSF receptor. Since the α subunit is specific for the hGM-CSF receptor, as opposed to the β subunit, the antibodies to the a subunit also determine the presence of the receptor. One can use any of the antibodies described herein. For example, the antibody and an iodinated avin. In one embodiment, one uses a cocktail of the different antibodies. Alternatively, one can use one of the antibodies with a second labelled-antibody such as an anti-mouse antibody. In another embodiment, one can use a biotinylated antibody with a second label such as using biotinylated anti-GM-CSF receptor antibody. Such an antibody can be prepared by standard means, for example, by reaction of the antibody with NHS-LC-Biotin, and strepavidin allophycocyin. By such a system one can test receptor expression by three color sorting. This permits a simple means to determine whether, for example, a stem cell fraction such as CD34$^+$CD38$^-$ cells or a progenitor cell fraction such as CD34$^+$ CD38$^+$, differ in expression of receptor. Other methods of testing cells to determine receptor expression can also be used. For example, autoradiography such as by iodinated antibody or iodinated strepavidin. Other assay methods using these antibodies are known such as a modification of that described by Koyama, H., et al., *Anal. Biochem.* 205:213–219 (1992).

These antibodies can also be used to deliver a target molecule to a desired cell expressing hGM-CSF receptors. For example one can conjugate the antibody to a cytotoxic molecule for example, a ricin molecule, to kill a target cell. Ricin can be linked to one of the described monoclonal antibodies by a number of means, such as using a non-reducible thioester bond using the methodology of Youle, E. J., *Proc. Natl. Acad. Sci. USA* 77:5483–5486 (1980). In another embodiment one can couple the protein to the desired molecule by a polylysine-conjugate adapting the methodology of Wu & Wu, *J. Biol. Chem.* 262:4429–4432, (1987). These conjugated antibodies can also be used to inhibit or kill the growth AML blasts which express the receptor. Thus this methodology should be useful in inhibiting or retarding leukemias as well as other diseases resulting from interaction of a molecule such as GM-CSF with the GM-CSF receptor.

The presence of the receptor and/or cells expressing the receptor can be determined by assaying for it using the antibodies as a probe. In one preferred embodiment, one would use a quantitative immunoassay procedure. For example, one can determine whether the level of receptor on cells or in the body has increased or decreased when a treatment has begun. Thus, one can compare results against baseline levels obtained from the materials being sampled. Further, one can take samples from the same individual at various times to monitor continuing levels of expression.

The soluble GM-CSF receptor may be detectable in body fluids such as blood, serum, plasma, urine, cerebrospinal fluid, supernatant from cell lysate breast aspirates and body tissues using these antibodies.

These antibodies can be used to determine the amount of receptor in a sample by contacting the sample, either body fluid or tissue, with at least one of the antibodies, preferably a monoclonal antibody, and determining whether binding has occurred. Preferably, one quantifies the amount of binding that occurs. As aforesaid, immunoreactive fragments of these antibodies can also be used and are included within the definition of antibody as used herein.

The GM-CSF receptor may be differentially expressed in normal and maliganant cells. Tumors expressing the highest levels of receptor frequently are derived from cells which express high levels of cellular proteins and receptors. Thus, one can locate tumors by looking for high levels of binding of the present antibody. Then, by monitoring the level of receptor expression one can determine the most appropriate therapy.

For example, GM-CSF interacts with cells via the GM-CSF receptors. High levels of GM-CSF have been shown to be involved in the establishment and progression of myeloid leukemias. Furthermore, its activity in synovial fluid in patients with rheumatoid arthritis suggest that the GM-CSF receptor is implicated in the etiology of this disorder. Various tumor cell lines of non-hematopoietic origin have been described as being responsive to GM-CSF. For example, small cell carcinoma of the lung, breast carcinoma cell lines, and SV40 transformed marrow stromal cell line, adenocarcinoma cell lines, tumors of neuroendocrine phenotype and neural crest origin, including malignant melanoma. Thus, by looking for the presence of receptor for GM-CSF on such cell lines, and comparing such levels of expression with a baseline one can determine differences. In addition, one can monitor progression of conditions by comparing the level of expression at different times. Human endothelial cells, trophoblast cells and placenta also express the receptor. The role of GM-CSF may also be important in the development of birth disorders. These antibodies provide a simple means for assaying for the effects of differing amounts of hGM-CSF and receptor on such conditions.

Furthermore, one can take advantage of the receptors being present on such cell lines to deliver a desired target molecule such as the above-described cytotoxic molecules. In addition, one can use these antibodies to block such receptors to retard and/or inhibit the effect of GM-CSF on such conditions in these cell lines.

These antibodies can be used to locate, monitor and/or isolate cells in vivo which differentially express GM-CSF receptor. For example, the antibody can be labeled with a radionuclide, e.g., 111-indium. The labelled antibody can then be injected intravenously and scanned to determine where the labelled antibody accumulates. Typically, it will differentially accumulate in cells producing high levels of receptor. The amount of labeled antibody can readily be determined based upon the present disclosure, and methods for scanning are well known in the art. For example, one can use a scintegraphic camera for scanning. By looking for cells having antibody binding, one can detect cells expressing receptor, isolation can be accomplished by standard techniques.

In accord herewith, the presently described antibody or a cocktail of probes including antibodies to other proteins that one wishes to monitor at the same time such as a protein produced by and associated with a tumor can be used for detection. The antibody probes can be labeled directly with a reporter or indirectly with a specific binding pair using conventional techniques.

Specific binding pairs can be of the immune or non-immune type. Immune specific binding pairs are exemplified by antigen-antibody systems of hapten/anti-hapten systems. These include fluorescein/anti-fluorescein, dinitrophenyl/anti-dinitrophenyl, biotin/anti-biotin, peptide/anti-peptide and the like.

Non-immune binding pairs include systems wherein the two components share a natural affinity for each other but are not antibodies. Exemplary non-immune pairs are biotin-streptavidin, intrinsic factor-vitamin $B_{12}$, folic acid-folate binding protein and the like.

A variety of methods are available to covalently label antibodies with members of specific binding pairs. Methods are selected based upon the nature of the member of the specific binding pair, the type of linkage desired, and the tolerance of the antibody to various conjugation chemistries. Biotin can be covalently coupled to antibodies by utilizing commercially available active derivatives. Some of these are biotin-N-hydroxy-succinimide which binds to amine groups on proteins; bitoin hydrazide which binds to carbohydrate moieties, aldehydes and carboxyl groups via a carbodiimide coupling; and biotin maleimide and iodoacetyl biotin which bind to sulfhydryl groups.

Fluorescein can be coupled to protein amine groups using fluorescein isothiocyanate. Dinitrophenyl groups can be coupled to protein amine groups using 2,4-dinitrobenzene sulfate or 2,4-dinitrofluorobenzene. Other standard methods of conjugation can be employed to couple monoclonal antibodies to a member of a specific binding pair including dialdehyde, carbodiimide coupling, homofunctional crosslinking, and heterobifunctional crosslinking. Carbodiimide coupling is an effective method of coupling carboxyl groups on one substance to amine groups on another. Carbodiimide coupling is facilitated by using the commercially available reagent 1-ethyl-3-(dimethyl-aminopropyl)-carbodiimide (EDAC).

Homobifunctional crosslinkers, including the bifunctional imidoesters and bifunctional N-hydroxy-succinimide esters, are commercially available and are employed for coupling amine groups on one substance to amine groups on another. Heterobifunctional crosslinkers are reagents which possess different functional groups. The most common commercially available heterobifunctional crosslinkers have an amine reactive N-hydroxysuccinimide ester as one functional group, and a sulfdhydryl reactive group as the second functional group. The most common sulfhydryl reactive groups are maleimides, pyridyl disulfides and active halogens. One of the functional groups can be a photoactive aryl nitrene, which upon irradiation reacts with a variety of groups.

The detectably-labelled probe, e.g., antibody, detectably-labelled antibodies, or detectably-labelled member of the specific binding pair is coupled to a reporter which can be a radioactive isotope, enzyme, fluorogenic, chemiluminescent or electrochemical materials. Commonly used radioactive isotopes are $^{125}I$, $Tc^{99m}$ and $^3H$. Standard radioactive isotopic labeling procedures include the chloramine T, lactoperoxidase and Bolton-Hunter methods for $^{125}I$ and reduction methylation for $^3H$.

Enzymes suitable for use in this invention include, but are not limited to, horseradish peroxidase, alkaline phosphatase, β-galactosidase, glucose oxidase, luciferase, β-lactamase, urease and lysozyme. Enzyme labeling is facilitated by using dialdehyde, carbodiimide coupling, homobifunctional crosslinkers and heterobifunctional crosslinkers as described above for coupling an antibody with a member of a specific binding pair.

The labeling method chosen depends on the functional groups available on the enzyme and the material to be labeled, and the tolerance of both to the conjugation conditions. The labeling method used in the present invention can be one of, but not limited to, any conventional methods currently employed including those described by Engvall and Pearlmann, *Immunochemistry* 8:871 (1971), Avrameas and Ternynck, *Immunochemistry* 8:1175 (1975), Ishikawa et al., *J. Immunoassay* 4 (3):209–327 (1983) and Jablonski, *Anal. Biochem.* 148:199 (1985), which are incorporated by reference.

Labeling can be accomplished by indirect methods such as using spacers or other members of specific binding pairs. An example of this is the detection of a biotinylated antibody with unlabelled streptavidin and biotinylated enzyme, with streptavidin and biotinylated enzyme being added either sequentially or simultaneously. Thus, according to the present invention, the antibody used to detect can be detectably-labelled directly with a reporter or indirectly with a first member of a specific binding pair. When the antibody is coupled to a first member of a specific binding pair, then detection is effected by reacting the antibody-first member of a specific binding complex with the second member of the binding pair which is labelled or unlabelled as mentioned above.

Moreover, the unlabelled detector antibody can be detected by reacting the unlabelled antibody with a labelled antibody specific for the unlabelled antibody. Such an anti-antibody can be labelled directly or indirectly using any of the approaches discussed above. For example, the anti-antibody can be coupled to biotin which is detected by reacting with the streptavidin-horseradish peroxidase system discussed above.

One preferred embodiment utilizes biotin. The biotinylated antibody is in turn reacted with streptavidin-horseradish peroxidase complex. Orthophenylenediamine, 4-chloro-naphthol, or tetramethylbenzidine (TMB) can be used to effect chromogenic detection.

The preferred immunoassay format for practicing this invention is a forward sandwich assay in which the capture reagent has been immobilized, using conventional techniques, on the surface of the support. Suitable supports used in assays include synthetic polymer supports, such as polypropylene, polystyrene, substituted polystyrene, e.g., aminated or carboxylated polystyrene; polyacrylamides; polyamides; polyvinylchloride, etc.; glass beads; agarose; nitrocellulose, etc.

The present antibody as discussed can also be used therapeutically as a carrier for drugs, biologically and chemically produced toxins or cytotoxic agents. These antibodies will differentially locate cells expressing high levels of GM-CSF receptor and are an effective method of delivery. The drugs, toxins and cytotoxic materials can be attached to the antibody in the same manner as the other labels resulting in a coupled conjugate. Such coupled antibody conjugates, preferably monoclonal antibody conjugates may also be used to deplete a target such as bone marrow or peripheral blood of such cells (i.e., ex vivo depletion) prior to autologous bone marrow transplantation.

The antibody or peptide can be delivered by any of a number of means. For example, either can be administered by parenteral injection (intramuscular (i.m.), intraperitoneal (i.p.), intravenous (i.v.) or subcutaneous (s.c.)), oral or other routes of administration well known in the art. Parenteral administration is preferred.

The amount used will typically be in the range of about 0.1 mg to about 10 mg/kg of body weight. The antibodies and peptides will preferably be formulated in a unit dosage form.

For example, solid dose forms that can be used for oral administration include capsules, tablets, pills, powders and granules. In such solid dose forms, the active ingredient, i.e., antibody or peptide, is mixed with at least one inert carrier such as sucrose, lactose or starch. Such dose forms can also comprise additional substances other than inert diluents, e.g., lubricating agents, such as magnesium stearate. Furthermore, the dose forms in the case of capsules, tablets and pills may also comprise buffering agents. The tablets, capsules and pills can also contain time-release coatings.

For parenteral administration, one typically includes sterile aqueous or non-aqueous solutions, suspensions or emulsions in association with a pharmaceutically acceptable parenteral vehicle. Examples of non-aqueous solvents or vehicles are propylene glycol, polyethylene glycol, vegetable oils such as olive oil and corn oil, gelatin and injectable organic esters, such as ethyl oleate. These dose forms may also contain adjuvants such as preserving, wetting, emulsifying and dispersing agents. They may be sterilized by, for example, filtration through a bacterial-retaining filter, by incorporating sterilizing agents into the composition, by irradiating the compositions, etc., so long as care is taken not to inactivate the antibody. They can also be manufactured in a medium of sterile water or some other sterile injectable medium before use. Further examples of these vehicles include saline, Ringer's solution, dextrose solution and 5% human serum albumin. Liposomes may also be used as carriers. Additives, such as substances that enhance isotonicity and chemical stability, e.g., buffers and preservatives, may also be used.

The preferred range of active ingredient in such vehicles is in concentrations of about 1 mg/ml to about 10 mg/ml. More preferably, about 3 mg/ml to about 10 mg/ml.

The present invention is further illustrated by the following examples. These examples are provided to aid in the understanding of the invention and are not to be construed as a limitation thereof.

Production of Anti-GM-CSF Receptor α Monoclonal Antibody

Expression of Cells containing A Human GM-CSF Receptor

FDCP1 cells [Dexter, T. M., et al., *J. Exp. Med.* 152:1036–1047 (1980)] were electroporated with linear constructs of 60 μgm of $\alpha_2$ receptor subunit [Crosier K., et al., *Proc. Natl. Acad. Sci. USA* 88:7744–7748 (1991)] and 6 μgm of the neomycin resistance gene both in the vector pmt21 at 980 μF and 275 volts with the time constant set by the apparatus (Gene Pulser, Bio-Rad, Richmond, Calif.). The electroporated cells were first selected for their ability to grow in 1 mg/ml G418 (GIBCO, Grand Island, N.Y.) and then in $1\times10^{-8}$ M human GM-CSF. The cells were then subjected to fluorescence activated cell sorting (FACS, Becton-Dickinson, Rutherfore, N.J.) with phycoerythrin-labelled hGM-CSF (R and D Systems, Minneapolis, Minn.) according to the directions of the manufacturer, except that the number of cells used was doubled. Cells that expressed high levels of α receptor (top 5–7%) were collected, expanded in the presence of hGM-CSF, and resorted 3 additional times to isolate cells with the highest receptor expression. Scatchard analysis using $^{125}$I-GM-CSF (New England Nuclear, Boston, Mass.) binding to these cells demonstrated receptor expression in excess of 100,000 sites/cell.

Production of Antibodies to GM-CSF Receptor α Subunit

The FDCP1 cells expressing high levels of α subunit (FDC-GMRα) were irradiated with 4,000 cGy and $1-2\times10^5$ cells were injected intraperitoneally without adjuvant into DBA/2 mice every 4–6 weeks. After the fourth injection, the mice were checked for anti-α titers on FDC-GMRα by FACS using fluorescein isothiocyanate (FITC)-labelled goat anti-mouse Ig $Fab_2$ (Organon Tecknika, Durham, N.C.). An additional boost of FDC-GMRα was given both intravenously and intraperitoneally prior to the fusion.

Production of Monclonal Antibodies

Spleens from 3 mice with the highest titers were fused to NSI myeloma cells (American Type Culture Collection, Manassas, Va.) by stirring in the presence of 50% PEG 1500 (Boehringer-Mannhein, Indianapolis, Ind.). The resulting hybridomas from each fusion were plated into twenty 96-well plates and were selected with HAT medium. All single-cell colonies were screened for the production of antibody that bound to FDC-GMRα but not to wild-type, non-transfected FDCP1 cells. All colonies meeting this criteria were then single-cell cloned two more times by limiting dilution. All subclones scored positive for anti-GMRα antibody production by FACS analysis. Antibodies expressed by five of these hybridoma were designated 1.013A1, 207E1, 4A4C1, 11E7A1, and 12E7A1. The 5 hybridomas expressing antibodies that were specific for human GM-CSF receptor a subunit were deposited with the American Type Culture Collection (ATCC), 10801 University Boulevard, Manassas, Va. 20110-2209, pursuant to the Budapest Treaty and given Accession Numbers HB 11198, HB 11194, HB 11195, HB 11197, and HB 11196, respectively.

The FDCP1 cells ($5\times10^5$) expressing high levels of the GM-CSF receptor and wild-type FDCP1 cells, ($5\times10^5$) were incubated with tissue culture supernatant (0.1 ml) from hybridoma cells producing the antibodies for 1 hour at 4° C. The cells were washed and then incubated with fluorescein-labelled goat antimouse Ig $Fab_2$ fragment and subjected to FACS analysis. FIGS. 1A–C shows the different patterns of binding that were observed. In FIG. 1A, a low intensity binding was observed. FIG. 1B, a medium level of binding was observed and FIG. 1C, a high level of binding was observed.

Effect of Antibody On Cell Proliferation

Figure 2:
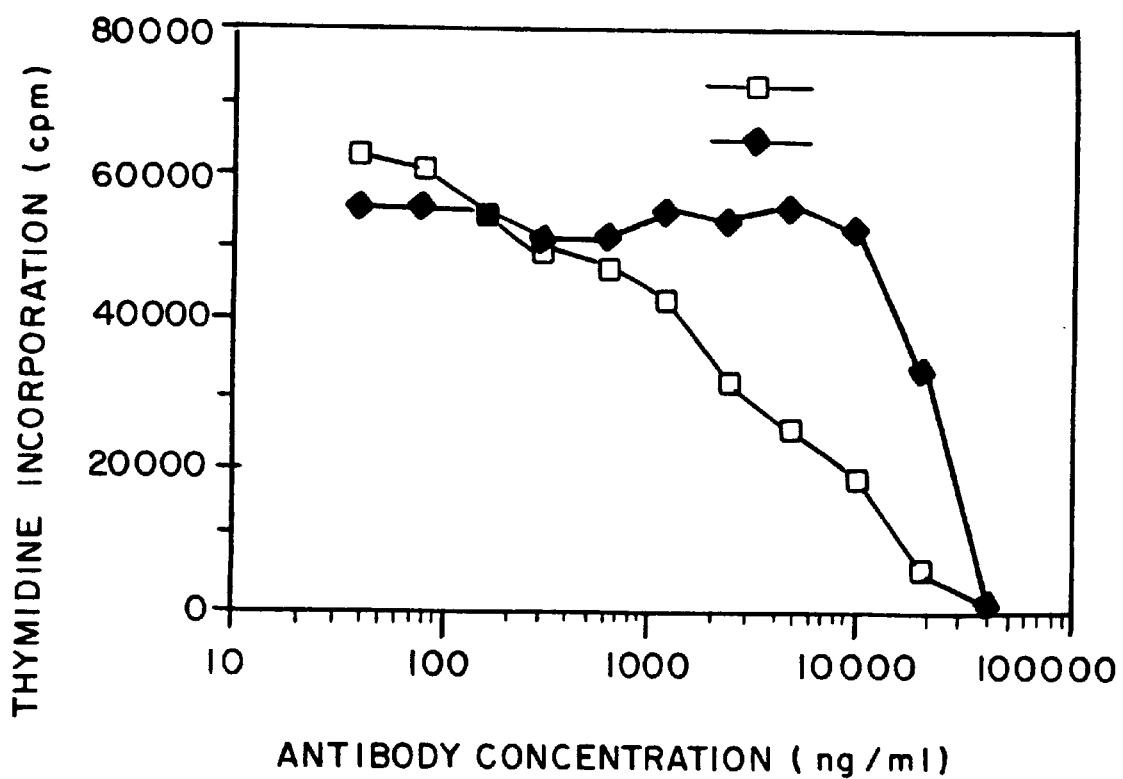
FIG. 2 shows the effect of the antibody on cell proliferation.

The FDCP1 transfected cells (3000 cells/well) were cultured in the presence of either human GM-CSF (square in FIG. 2) or 10% WEHI condition media, which is a source of murine, IL-3 (diamond in FIG. 2) at the indicated concentrations for a pool of 5 purified antibodies for 36 hours at 37° C. degrees. The cells were then labelled for 4 hours with $^3$H-thymidine and the incorporated thymidine was measured. The results are shown in FIG. 2.

The above-described procedure was repeated using the 5 antibodies individually, either purified or not, i.e. the crude antibodies. These results show that all the individual antibodies were inhibitory.

In addition, the above-described procedure was repeated with the individual antibodies, either crude or purified, with the human GM-CSF dependent cell line TF-1 and MO7 as well as the murine factor dependent cell line BA-F3 which expresses functional transfected hGM-CSF receptors. The growth of these cell lines was also inhibited in the presence of GM-CSF, but not IL-3.

The antibody pool was able to inhibit the growth of human progenitor cells. Human bone marrow was obtained from healthy donors after informed consent. The mononuclear cells were isolated by centrifugation through Ficoll-Paque (Pharmacia) at 400 g for 40 minutes at room temperature. The cells were next incubated in Iscove's modified Dulbecco's medium (IMDM) supplemented with 15% fetal calf serum (FCS) for 2 hours at 37° C. in tissue culture disks and the non-adherent cells were collected. The mature hematopoietic cells were removed by incubating the cells in monoclonal antibodies against CD2, CD5, CD11b, CD15, and CD19 as well as the My8 & 10F7 antibodies for 30 minutes at 4° C. The labelled lineage-positive cells were separated with a magnet and the remaining lineage-negative progenitor cells were saved. The progenitor cells were plated ±20 μg/ml of pooled antibody in serum-free methylcellulose cultures at $10^3$ cells/well. These cultures contained stem cell factor (50 ng/ml) and GM-CSF (12 pM) or IL-3 (12 pM). The results are the mean number of granulocyte and macrophage colonies from two dishes assayed after three weeks in culture.

|  | GM-CSF | | IL-3 | |
|---|---|---|---|---|
| Antibody | + | − | + | Gl |
| Colonies | 5.0 | 14.0 | 20 | 16 |

Figure 4:
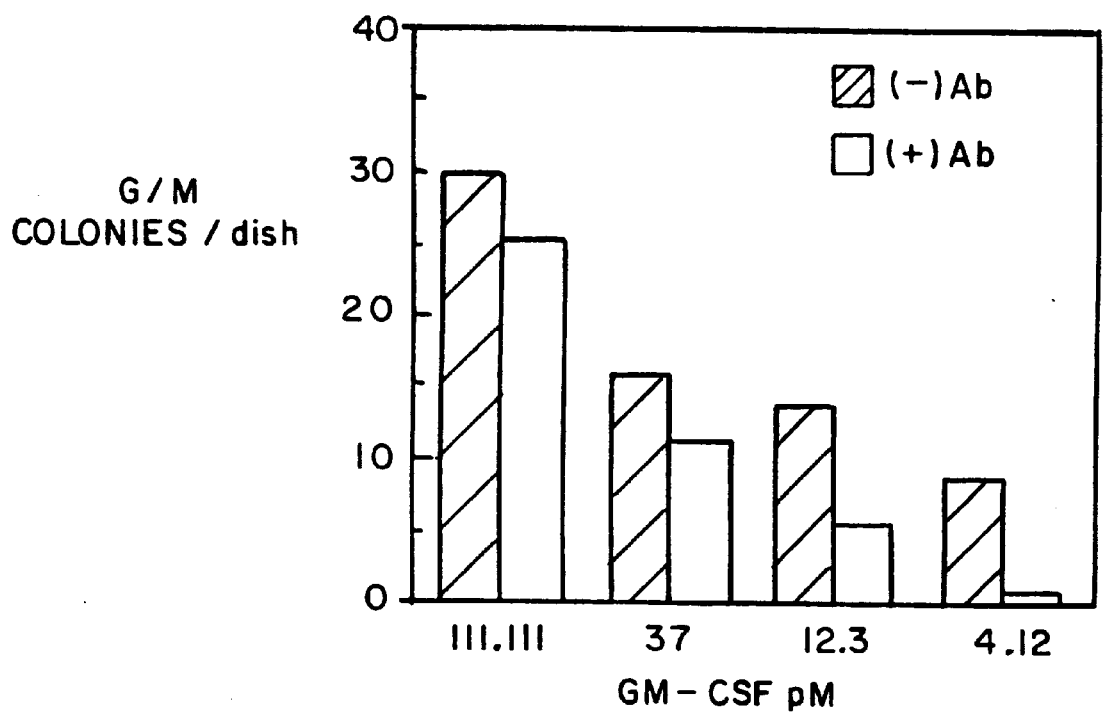
FIG. 4 shows inhibition of granulocyte macrophage colony formation by an antibody according to the present invention.

The above procedure was repeated except the pooled cultures contained varying concentration of GM-CSF as indicated in FIG. 4.

The experiment performed above was also done in the presence of varying concentrations of GM-CSF. The results are shown in FIG. 4.

The inhibition of proliferation on these cells by the antibody appears to result, at least in part from blocking of ligand binding. The binding of GM-CSF to cells has been demonstrated to be inhibited by a pool of the purified antibodies. Alternatively, some of the antibodies may act at a site separate from ligand binding to cause the inhibitory effects.

Purification of Receptor

Figure 3:
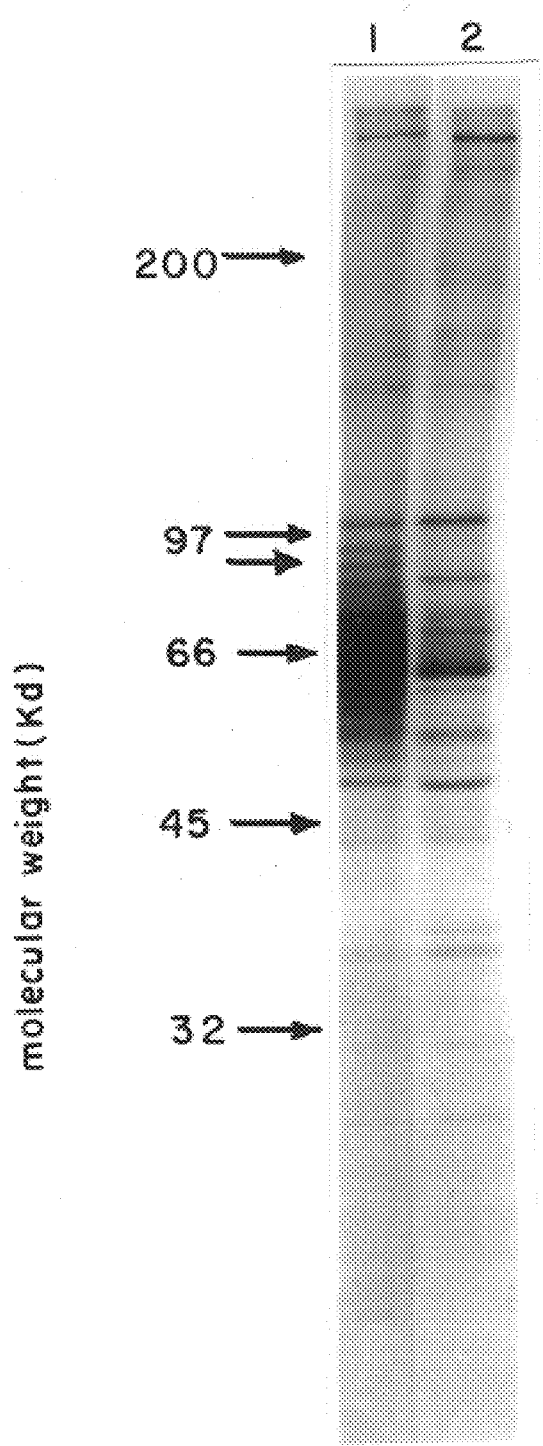
FIG. 3 is an autoradiograph showing immunoprecipitation of the $\alpha_1$ subunit from transfected COS cells.

COS cells were transiently transfected with GM-CSF receptor α subunit using the DEAE dextran technique. 48 hours later, they were incubated in the presence of 400 μC/ml $^{35}$S-methionine for 8 hours at 37° C degrees. The cells were then solubilized in 1% Triton, 30 mM Tris pH 8.0, 150 mM NaCL and protease inhibitors. A purified pool of the 5 antibodies was added to a final concentration of 30 μgm/ml for 2 hours at 4° C. degrees and the complex was precipitated with sepharose-linked antimouse Ig immunoglobulin. The resulting material was eluted with SDS sample buffer and labelled on a 7–13% acrylamide gradient gel and subjected to autoradiography. See FIG. 3. Lane 1 shows immunoprecipitation of cells transfected with the a subunit receptor. Lane 2 shows immunoprecipitation of a mock-transfected cell. The bold arrow indicates a band in lane 1, not present in lane 2, which has the expected molecular weight of the a subunit receptor. The low molecular weight region (50–70 kD) of lane 1, which has an increased intensity over that observed in lane 2, probably represents partially processed receptor.

Inhibition of $^{125}$I-GM-CSF Binding

The FDCP1 cells expressing the human GM-CSF α subunit receptor were incubated in the presence of the indicated concentration of $^{125}$I-GM-CSF with or without 150-fold excess of unlabelled GM-CSF and with or without 30 μg/ml of pooled antibody for 5 hours at 4°. See, Table 1, supra. The cells were then centrifuged through 100% fetal calf serum and the pellet counted on a gamma counter. The results are set forth in Table 1.

It is evident that those skilled in the art given the benefit of the foregoing disclosure may make numerous modifications thereof and departures from the specific embodiments described herein without departing from the inventive concepts and the present invention is to be limited solely by the scope and spirit of the appended claims.

I claim:

1. A hybridoma selected from the group consisting of hybridoma 1.013A1 (HB 11198), 207E1 (HB 11196), 4A4C1 (HB 11195), 11E7A1 (HB 11197), and 12E7A1 (HB 11196).

2. The hybridoma of claim 1 which is 1.013A1 (HB 11198).

3. The hybridoma of claim 1 which is 207E1 (HB 11196).

4. The hybridoma of claim 1 which is 4A4C1 (HB 11195).

5. The hybridoma of claim 1 which is 11E7A1 (HB 11197).

6. The hybridoma of claim 1 which is 12E7A1 (HB 11196).

* * * * *

UNITED STATES PATENT AND TRADEMARK OFFICE
CERTIFICATE OF CORRECTION

PATENT NO : 5,932,704
DATED : August 3, 1999
INVENTOR(S) : Paul T. Jubinsky

It is certified that error appears in the above-identified patent and that said Letters Patent are hereby corrected as shown below:

Col. 1, before line 4, insert --The above invention was made, in part, with support from Grant No. GM13452 and the United States Government has certain rights thereto--.

Col. 13, line 3, replace "(HB 11196) with --(HB 11194)--.

Col. 13, line 8, replace "(HB 11196)" with --(HB 11194)--.

Signed and Sealed this

Fourth Day of April, 2000

Q. TODD DICKINSON

*Attest:*

*Attesting Officer*    *Director of Patents and Trademarks*